(12) United States Patent
Srinivasan

(10) Patent No.: US 6,334,863 B1
(45) Date of Patent: Jan. 1, 2002

(54) APPARATUS AND METHOD PROVIDING AN INSERTION MEDICAL DEVICE

(75) Inventor: Murli Srinivasan, Duluth, GA (US)

(73) Assignee: Rusch, Inc., Duluth, GA (US)

(*) Notice: Subject to any disclaimer, the term of this patent is extended or adjusted under 35 U.S.C. 154(b) by 0 days.

(21) Appl. No.: 09/532,701

(22) Filed: Mar. 22, 2000

(51) Int. Cl.⁷ .............................................. A61M 29/00
(52) U.S. Cl. ...................................................... 606/191
(58) Field of Search ................................. 606/191, 195, 606/192, 194, 104, 270, 1

(56) References Cited

U.S. PATENT DOCUMENTS 4,516,970 A * 5/1985 Kaufman et al. ........... 604/270
4,726,373 A * 2/1988 Greengrass ................. 128/343
4,874,365 A * 10/1989 Frederick et al. ............. 604/54
5,366,471 A * 11/1994 Jones et al. ................. 606/191

* cited by examiner

Primary Examiner—Kevin Truong
(74) Attorney, Agent, or Firm—St. Onge Steward Johnston & Reens LLC

(57) ABSTRACT

This invention provides an apparatus and method for an insertion medical device that dilates internal strictures. The insertion medical device includes a flexible dilator having an enclosed, hollow chamber substantially filled with crystalline tungsten powder. More particularly, a bougie is disclosed. The crystalline tungsten powder provides the bougie with improved flowability and performance when placing the bougie in the stricture. In another aspect, the invention provides improved flowability and adequate weight to other medical devices such as feeding tubes and endoscopy instruments.

19 Claims, 1 Drawing Sheet

APPARATUS AND METHOD PROVIDING AN INSERTION MEDICAL DEVICE

FIELD OF THE INVENTION

This invention relates to an insertion medical device and, more particularly, to hollow rubber dilators filled with flowable material for treating constricted, internal passageways.

BACKGROUND OF INVENTION

Stenosis, or esophageal stricture, is a narrowing or constricting of the diameter of a patient's esophagus and prevents the normal peristaltic activities of the esophagus. It may impede the patient's ability to swallow and/or block access to the digestive tract. Treatment often requires dilation of the esophagus at its junction with the stomach.

As noted in U.S. Pat. No. 5,366,471, there are several esophageal dilators known in the art. One such dilator is a bougie having a hollow, central channel extending the length of the bougie, for insertion of a guide wire previously placed in the patient. This type of dilator is most often used with tight strictures that are 1.2 centimeters, or less, in diameter. Another type of dilator is a wire-guided balloon dilator. The guide wire locates the balloon in the stricture and, thereafter, the balloon is slowly inflated. The balloon dilator is best used in asymmetrical strictures that are 1.2 centimeters, or more, in diameter.

Another type of esophageal dilator is the Mercury-filled rubber bougie. The bougie comprises a rubber sheath filled with Mercury, and having a tapered tip. The bougie is inserted, tip-first, through a patient's mouth and into the esophagus, applying light pressure to enlarge the diameter of the stricture. The rubber bougie is best used in treating strictures which are symmetrical and more than 1.2 centimeters in diameter. Since most esophageal strictures meet these requirements, the rubber bougie is the most commonly used esophageal dilator.

The Mercury core provides the weight necessary for proper performance of the dilator, and, because Mercury is liquid at ambient and body temperatures, it allows flexing of the dilator.

Ribs can form in the surface of a rubber dilator at the location of a tight bend, and can cause damage to the interior lining of the patient's esophagus. The Mercury core also prevents ribs from forming in the outer surface of the sheath at the location of a tight bend.

One disadvantage to the use of Mercury as the core of a rubber bougie is that Mercury is toxic to humans. The quantity of Mercury held in a bougie could result in a fatality if it were to escape into the patient. The flowability of liquid Mercury enhances the danger, since even a small crack in the sheath of the bougie could result in leakage of the entire quantity of Mercury leaking out of the bougie and into the patient's mouth, esophagus or stomach. If Mercury enters the bloodstream, it can cause mercury poisoning. In addition, the physical action of a large quantity of Mercury on the digestive tract can cause severe effects. Thus, there are significant health risks associated with the use of Mercury.

U.S. Pat. No. 5,366,471 ("the '471 patent") discloses an esophageal dilator where instead of using Mercury, a solution of Tungsten powder suspended in silicone is used. This invention seeks to achieve the benefits of Mercury but without the health risks. The '471 patent teaches that the Tungsten powder, if not suspended in silicone, may cake up, or pack together, forming clumps. The '471 patent teaches that Tungsten powder, if not suspended in silicone, may not have adequate flowability properties and ribs may form in the bougie and this could damage the patient's esophagus. However, one disadvantage of the suspension of Tungsten in silicone claimed in the '471 patent is that the silicone fluid has the potential of leakage in the event the bougie is cracked.

What is desired, therefore, is a medical device that is filled with a material that possesses adequate flowability properties such that, when inserted into a constricted, internal passageway, the device does not form ribs and can be easily maneuvered to effect dilation. What is also desired is that the material substantially fill the bougie in order to allow the bougie to be inserted deep into the passageway and still maintain adequate weight for maneuverability and to be free from forming ribs throughout the bougie. What is further desired is a material that would not easily flow from a damaged or cracked bougie into the patient's body.

SUMMARY OF INVENTION

Accordingly, it is the object of this invention to provide an apparatus and method for making an insertion medical device.

It is another object to provide an apparatus for dilating internal strictures using a flexible tube of adequate weight and flowability comprising crystalline tungsten powder.

It is another object to provide a bougie comprising crystalline tungsten powder for dilating internal strictures wherein, while maneuvering through narrow and curved passageways, said bougie maintains a smooth, uninterrupted surface free from creases.

It is another object to make an apparatus that provides adequate weight and flowability to facilitate the use of other insertion devices such as feeding tubes and endoscopy instruments.

Yet another object is to provide a method for making a bougie substantially filled with crystalline tungsten powder.

These and other objects of the invention are achieved by an apparatus and method for making an insertion medical device comprising a flexible, silicone rubber tube with a tapered tip; said flexible, silicone rubber tube having an enclosed, hollow space; and crystalline tungsten powder substantially filling said enclosed, hollow space.

DETAILED DESCRIPTION

Preferred embodiments of the invention will be described in detail with reference to FIGS. 1–2 attached hereto.

Figure 1:
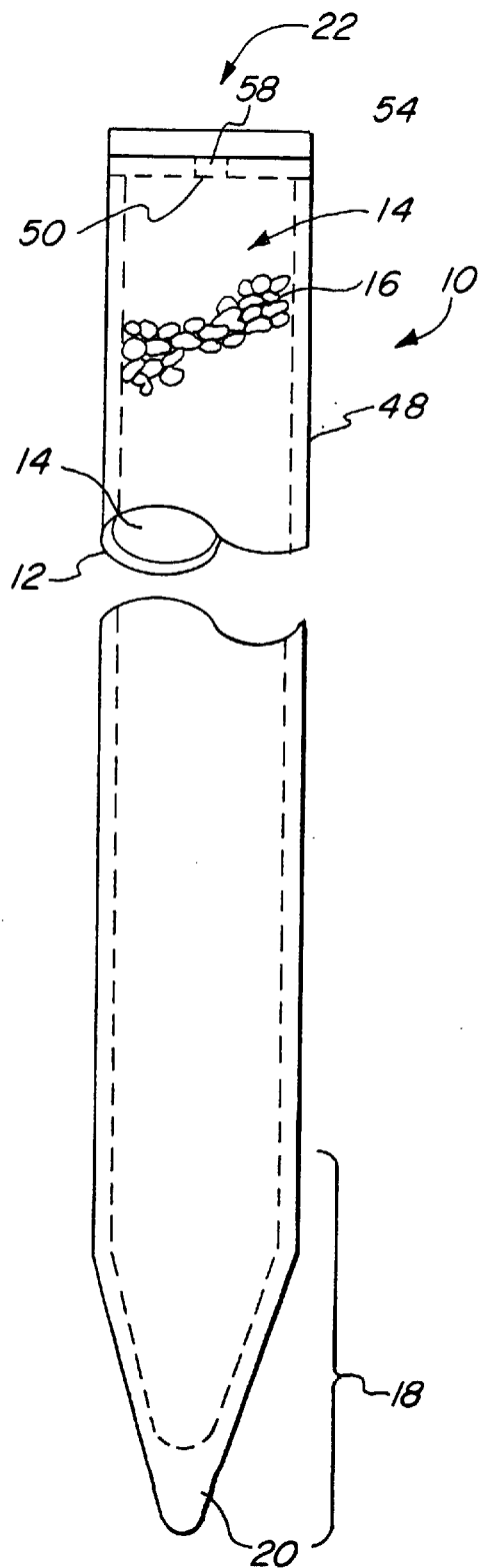
FIG. 1 is side view of the insertion medical device.

The embodiment shown in FIG. 1 depicts an insertion medical device 10 for dilating internal strictures comprising a tube 12 having requisite flexibility and an enclosed, hollow space 14 substantially filled with crystalline tungsten powder 16.

In the preferred embodiment, the tube 12 is made of a flexible and waterproof material, such as silicone rubber. Flexibility is desired because the tube 12 must conform to the curves and tight bends normally found in internal passageways. Further, a flexible tube would be most comfortable for the patient. In the past, some esophageal bougies had metal guide wires within the tube for facilitating placement of the tube 12 inside the passageway, and that this caused pain to the patient; thus, in the preferred embodiment, such wires are omitted. A waterproof material is used because it is desired to keep the internal medical device's 10 contents dry and separate from the patient's internal fluids. This prevents accidental toxicity and keeps the device working properly. Silicone rubber is used because it provides the necessary flexibility and waterproof properties.

Also in the preferred embodiment, the tube 12 is tapered at the distal end 20 to facilitate insertion into the internal stricture and has an enclosed, hollow space 14 that extends upwardly towards the proximal end 22. The enclosed, hollow space 14 will substantially extend the entire length of the tube 12 in order to allow crystalline tungsten powder 16 ("CTP") to be added to provide adequate weight to the flexible tube 12. Further, the enclosed, hollow space 14 will have a resealable opening through which the CTP 16 can be added and contained within the flexible tube 12.

CTP 16 is preferably used to substantially fill the enclosed, hollow space 14 because it has the necessary flow and weight characteristics to permit placement of the insertion medical device 10 while still maintaining sufficient flexibility in the tube 12.

CTP 16 is a crystallized form of tungsten and is not to be confused with regular tungsten powder. CTP particles are approximately 2 to 4 times larger than regular tungsten powder and have a body-centered cubic. Further, CTP 16 has a Hall Flow rate of approximately 6 to 10 seconds/50 grams in contradistinction to standard tungsten powder that does not exhibit any flow characteristic and cannot be measured using the Hall Flow test. In addition, CTP 16 has a rougher surface than standard tungsten powder and this prevents the tungsten from clumping or packing together. Because of the foregoing, CTP 16 possesses flowability properties not found in standard tungsten powder. Because of its flowability, CTP 16 is effective when used by itself. However, if desired, CTP 16 can be suspended in a fluid, such as silicone, in order to vary flowability.

CTP 16 has a Scott Density of approximately 140 to 160 grams/cc and this density has been found to be adequate for providing the necessary weight to the tube 12 in order to enable the user to maneuver the insertion medical device 10. The density further provides the firmness necessary to enable the physician to push upon the insertion medical device 10 to force open a constricted passageway without a guide wire.

CTP 16 is made by an alkaline process where tungsten powder is chemically enlarged. CTP 16 particles are in the shape of crystals and are approximately 40 to 75 microns. This large size is a factor in the CTP's favorable flow rate. Further, when the insertion medical device 10 is bent, the surface of the insertion medical device 10 remains free from creases and this reduces pain to the patient due to the non-clumping properties of the large size crystal. CTP 16 is also non-toxic to humans and makes CTP 16 more desirable for a rupture in the flexible tube 12 will not cause a health concern to the patient. In addition, because CTP 16 is preferably in a solid state, the CTP 16 will not rapidly exit via the rupture and enter the patient's body, thereby making CTP 16 a desirable product to be used in the insertion medical device 10.

In order to provide an insertion medical device 10 that is capable of dilating strictures deep within a passageway and to accommodate large individuals, the insertion medical device 10 should be at least 30 inches in overall length and have a uniform diameter typically in the range of 0.21 inches to 0.79 inches. The tip 18 is typically about 6 inches in length, with a rounded end having a diameter of approximately 0.19 inches and is tapered so that its outer surface smoothly meets the outer surface of the tube 10 at its distal end 20. Further, the CTP 16 should substantially fill the enclosed, hollow space 14 in order to provide adequate flowability that is necessary throughout the insertion medical device 10.

In the preferred embodiment, the insertion medical device 10 is a bougie. Alternatively, CTP 16 can be used with any flexible tube having a hollow chamber in order to provide adequate weight and flowability. The wide array of medical devices that can be produced using CTP 16 includes, but is limited to, feeding tubes and endoscopy instruments. It is envisioned that any instrument that is to be inserted requires adequate weight in order to be inserted within the human body. Further, such instrument requires adequate flowability from a non-toxic substance, yet firmness in order to facilitate maneuverability. All these advantages are provided with CTP 16 and this makes CTP 16 versatile and adaptable to a variety of instruments beyond the preferred embodiment.

Figure 2:
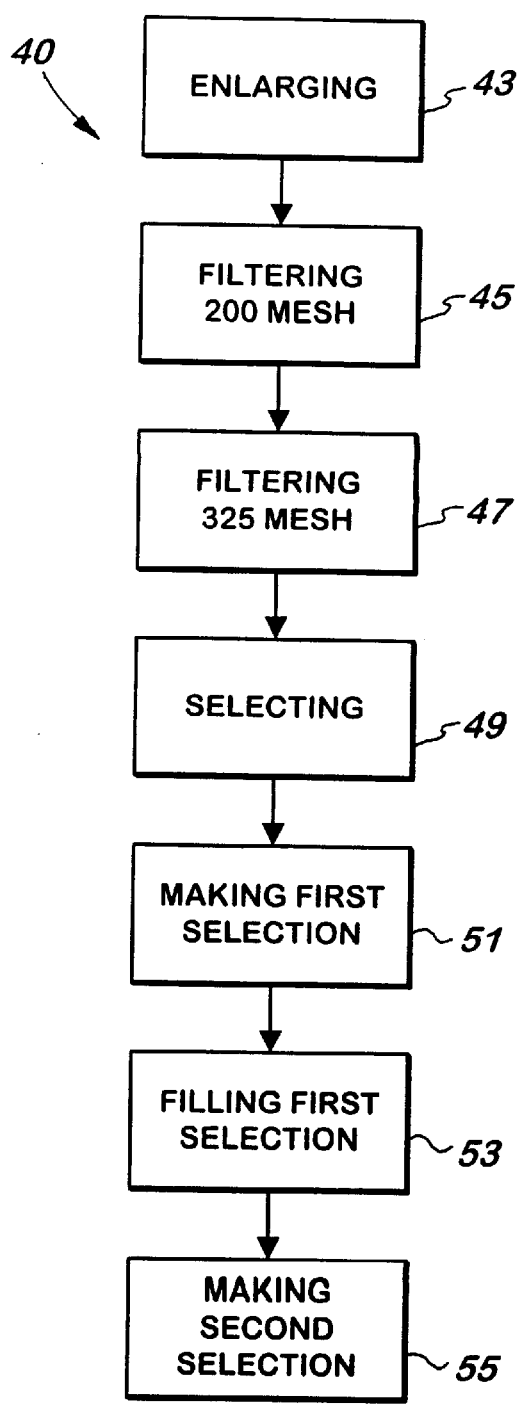
FIG. 2 is flowchart of the steps for making a bougie.

The embodiment shown in FIG. 2 depicts a process 40 for making a bougie 42 substantially filled with CTP 16 for dilating internal strictures. The process comprising: enlarging tungsten powder using an alkaline process to produce CTP 16 at 43, filtering the CTP 16 through a 200 mesh screen 44 at 45, again filtering the CTP 16 through a 325 mesh screen 46 at 47, selecting the CTP 16 not filtered through the 325 mesh screen 46 at 49, making a first section 48 of silicone rubber having an aperture 50 and an internal, hollow space 14 substantially the entire length of the first section 48 at 51, substantially filling said first section 48 with the selected CTP 16 that filtered through the 200 mesh screen 44 but not through the 325 mesh screen 46 at 53, and making a second section 54 of silicone rubber used to mate with and seal said aperture 50 at 55.

In the preferred embodiment, the first section 48 has a tapered tip at the distal end 20 and is made of silicone rubber. The first section 48 also includes an aperture 50 just large enough to allow CTP 16 to pass. The aperture should not exceed 3.0 mm and is preferably between 2.0 and 2.5 mm. This embodiment may be made by any of a number of methods including, but not limited to, injection molding, blow molding, and machining.

In the preferred embodiment, the second section 54 is also made of silicone rubber and may be made using the same method as for the first section 48. The second section 54 will ideally have a diameter equal to the first section 48 and will further comprise a portion that mates with the aperture 50 of the first section 48. Preferably, this mating portion is a male member 58 that has a diameter the same size as or larger than the diameter of the aperture 50. This will allow a tight fit to properly seal in the CTP 16 and ensure that no CTP 16 will leak out.

After filling the first section 48 with CTP 16, the second section 54 can then seal the aperture 50 permanently. It is preferred to permanently seal the aperture 50 because CTP 16 is not known to break down or decompose prior to the tube 12 being discarded for wear or sanitation purposes. Therefore, once a substantial amount of CTP 16 has been filled, there is no need to reopen the aperture 50. Hence, the first and second sections 48 and 54 may be sealed using a non-toxic sealant or other adhesive. Other methods of permanently sealing include, but are not limited to, ultrasonic welding, heating, and chemical bonding.

It is desirable to make the first and second sections 48 and 54 the same material because identical materials form the strongest bond upon sealing. Alternatively, similar materials may be used but this does not produce the strong bond identical materials form.

What is claimed is:

1. A medical device for dilating internal strictures comprising:
    a flexible tube having a distal end and a proximal end;
    said flexible tube having a tapered tip at said distal end and an enclosed, hollow space extending proximally from said tapered tip;
    said enclosed, hollow space extending proximally from said tapered tip being substantially filled with a crystalline tungsten powder of sufficient weight and flowability to permit placement of said medical device to effect dilation of an internal stricture;
    said crystalline tungsten powder having a Hall Flow rate of approximately 6 to 10 seconds/50 grams; and
    said crystalline tungsten powder having a Scott density of approximately 140 to 160 grams/cubic inch.

2. A medical device according to claim 1 wherein said enclosed, hollow space extending proximally from said tapered tip extends substantially along the entire length of said medical device.

3. A medical device according to claim 2 wherein said enclosed, hollow space extending proximally from said tapered tip being substantially filled with said crystalline tungsten powder such that said medical device can be inserted deep into an internal passageway and still maintain adequate weight and flowability for maneuverability and to be free from forming creases throughout said medical device.

4. A medical device according to claim 1 wherein a particle of said crystalline tungsten powder has a size of between approximately 40 to 75 microns.

5. A medical device for dilating internal strictures comprising:
    a flexible tube having a distal end and a proximal end;
    said flexible tube having a tapered tip at said distal end and an enclosed, hollow space extending proximally from said tapered tip; and
    said enclosed, hollow space extending proximally from said tapered tip being substantially filled with a crystalline tungsten powder of sufficient weight and flowability to permit placement of said medical device to effect dilation of an internal stricture.

6. A medical device according to claim 5 wherein said crystalline tungsten powder comprises a Hall Flow rate of approximately 6 to 10 seconds/50 grams.

7. A medical device according to claim 5 wherein said enclosed, hollow space extending proximally from said tapered tip extends substantially along the entire length of said medical device.

8. A medical device according to claim 7 wherein said enclosed, hollow space extending proximally from said tapered tip being substantially filled with said crystalline tungsten powder such that said medical device can be inserted deep into an internal passageway and still maintain adequate weight and flowability for maneuverability and to be free from forming creases throughout said medical device.

9. A medical device according to claim 5 wherein said crystalline tungsten powder has a scott density of approximately 140 to 160 grams/cubic inch.

10. A medical device according to claim 5 wherein a particle of said crystalline tungsten powder has a size of between approximately 40 to 75 microns.

11. A bougie for dilating laryngeal strictures comprising:
    a flexible tube having a distal end and a proximal end;
    said flexible tube having a tapered tip at said distal end and an enclosed, hollow space extending proximally from said tapered tip; and
    said enclosed, hollow space extending proximally from said tapered tip being substantially filled with crystalline tungsten powder in the absence of silicone fluid.

12. A bougie according to claim 11 wherein said enclosed, hollow space extending proximally from said tapered tip extends substantially along the entire length of said bougie.

13. A bougie according to claim 12 wherein said enclosed, hollow space extending proximally from said tapered tip being substantially filled with said crystalline tungsten powder such that said bougie can be inserted deep into an internal passageway and still maintain adequate weight and flowability for maneuverability and to be free from forming creases throughout said bougie.

14. A bougie according to claim 11 wherein said crystalline tungsten powder has a scott density of approximately 140 to 160 grams/cubic inch.

15. A bougie according to claim 11 wherein a particle of said crystalline tungsten powder has a size of between approximately 40 to 75 microns.

16. A bougie for dilating laryngeal strictures comprising:
    a flexible tube having a distal end and a proximal end;
    said flexible tube having a tapered tip at said distal end and an enclosed, hollow space extending proximally from said tapered tip;
    said enclosed, hollow space extending proximally from said tapered tip being substantially filled with a crystalline tungsten powder in the absence of silicone fluid;
    said enclosed, hollow space extending proximally from said tapered tip extends substantially along the entire length of said bougie;
    said enclosed, hollow space extending proximally from said tapered tip being substantially filled with said crystalline tungsten powder such that said bougie can be inserted deep into an internal passageway and still maintain adequate weight and flowability for maneuverability and to be free from forming creases throughout said bougie;
    said crystalline tungsten powder has a scott density of approximately 140 to 160 grams/cubic inch;
    a particle of said crystalline tungsten powder has a size of between approximately 40 to 75 microns; and
    said crystalline tungsten powder having a Hall Flow rate of approximately 6 to 10 seconds/50 grams.

17. A method for manufacturing a bougie comprising:
    enlarging tungsten powder to form a particles of crystalline tungsten powder between approximately 40 to 75 microns;
    screening said crystalline tungsten powder through a 200 size mesh screen;
    screening said crystalline tungsten powder through a 325 size mesh screen;
    selecting said crystalline tungsten powder not filtered through said 325 size mesh screen;
    molding a first section of silicone rubber having a tapered tip at a distal end, a hollow space extending proximally from said tapered tip and said hollow space substantially extending along the entire length of said first section, and a proximal end including an aperture;
    molding a second section of silicone rubber with a surface capable of mating and sealing said aperture of said first section and said second section of silicone rubber being used to enclose said hollow space extending proximally from said tapered tip;

filling said hollow space extending proximally from said tapered tip of said first section of silicone rubber with said crystalline tungsten powder;

fixedly placing said second section of silicone rubber on said aperture of said first section of silicone rubber, thereby enclosing said hollow space extending proximally from said tapered tip to form a bougie; and sterilizing said bougie.

18. The method according to claim 17 wherein said second section of silicone rubber forms an airtight and watertight seal with said first section of silicone rubber.

19. The method according to claim 17 wherein said first and second sections of silicone rubber together form a length of approximately 30 inches along the longitudinal axis.

* * * * *